US006620854B2

(12) United States Patent
Schnyder et al.

(10) Patent No.: US 6,620,854 B2
(45) Date of Patent: Sep. 16, 2003

(54) SURFACE-ACTIVE PREPARATIONS

(75) Inventors: Marcel Schnyder, Birsfelden (CH); François Brugger, Waltenheim (FR); Fernand Hoffstetter, Ranspach le Bas (FR); Karin Mühlbauer, Grenzach-Wyhlen (DE); Karin Petzold, Fischingen (DE); Radojka Vukomanovic, Basel (CH)

(73) Assignee: Ciba Specialty Chemicals Corporation, Tarrytown, NY (US)

( * ) Notice: Subject to any disclaimer, the term of this patent is extended or adjusted under 35 U.S.C. 154(b) by 0 days.

(21) Appl. No.: 09/885,346

(22) Filed: Jun. 19, 2001

(65) Prior Publication Data

US 2002/0032241 A1 Mar. 14, 2002

(30) Foreign Application Priority Data

Jun. 21, 2000 (EP) ........................................... 00810544

(51) Int. Cl.[7] ....................... A01N 31/14; A61K 31/075
(52) U.S. Cl. ....................................................... 514/717
(58) Field of Search .......................................... 514/717

(56) References Cited

U.S. PATENT DOCUMENTS 3,989,827 A * 11/1976 Apostaolatos et al. ...... 424/235
4,118,332 A 10/1978 Apostolatos et al. ....... 252/107
5,480,586 A 1/1996 Jakubicki et al. ........... 252/545
5,851,974 A 12/1998 Sandhu ........................ 510/235
6,107,261 A 8/2000 Taylor et al. ............... 510/131
6,204,230 B1 * 3/2001 Taylor et al. ............... 510/131

FOREIGN PATENT DOCUMENTS

| | | | |
|---|---|---|---|
| DE | 19530833 | | 2/1996 |
| WO | 96/06152 | | 2/1996 |
| WO | 97/46218 | | 12/1997 |
| WO | 9746218 | * | 12/1997 |

* cited by examiner

*Primary Examiner*—Alton N. Pryor
(74) *Attorney, Agent, or Firm*—Kevin T. Mansfield

(57) ABSTRACT

There are described surface-active soap compositions containing (a) from 0.01 to 2% by weight of an antimicrobial active ingredient from the class of diphenyl ethers, (b) from 0.1 to 30% by weight of a hydrotropic agent, (c) from 6.0 to 50% by weight of one or more synthetic detergents or soaps or a combination of such substances, (d) from 0 to 70% by weight of a monohydric or dihydric alcohol, and (e) tap water or deionised water ad 100%.

The composition is used for disinfecting and cleaning human skin and hands and hard objects, and in washing and cleaning formulations for textile fibre materials.

15 Claims, No Drawings

SURFACE-ACTIVE PREPARATIONS

The present invention relates to surface-active preparations, to the use thereof in disinfecting and cleaning human skin and hands and hard objects, and to the use thereof in washing and cleaning formulations for textile fibre materials.

Hydroxydiphenyl ethers are used as microbicidal active ingredients in household cleaning agents. Such formulations generally have high contents of synthetic detergents or soaps, which greatly reduce the bactericidal action of hydroxydiphenyl ether in the formulations, that is to say the bactericidal activity is unsatisfactory, but the formulations are known to have a very good long-term (persistent) microbiostatic activity on the treated surfaces (inanimate surfaces, such as textiles, plastics, carpets, tiles, etc.).

Surprisingly it has been found that, as a result of the addition of hydrotropic agents and/or alcohols, household cleaning formulations exhibit very strong bactericidal activity despite high contents of synthetic detergents or soaps.

The present invention accordingly relates to a surface-active preparation containing (a) from 0.01 to 2% by weight of an antimicrobial active ingredient from the class of diphenyl ethers, (b) from 0.1 to 30% by weight of a hydrotropic agent, (c) from 6.0 to 50% by weight of one or more synthetic detergents or soaps or a combination of such substances, (d) from 0 to 70% by weight of a monohydric or dihydric alcohol, and (e) tap water or deionised water ad 100%.

Soap compositions are to be understood as aqueous soap solutions. These may be in the form of soap solutions or so-called syndet solutions (=synthetic detergents).

The antimicrobial action of the preparation according to the invention extends to Gram-positive and Gram-negative bacteria as well as to yeasts, dermatophytes, etc.

As component (a) there come into consideration especially hydroxydiphenyl ethers of the general formula (1)

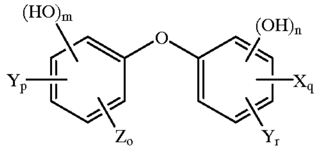

wherein

Y is chlorine or bromine,

X is $C_1$–$C_{20}$alkyl, hydroxy-substituted $C_1$–$C_{20}$alkyl, $C_5$–$C_7$cycloalkyl, hydroxy, formyl, acetonyl, $C_1$–$C_6$alkylcarbonyl, $C_2$–$C_{20}$alkenyl, carboxy, carboxy-$C_1$–$C_3$alkyl or carboxyallyl;

Z is hydrogen, hydroxy, $C_1$–$C_{20}$alkyl, $C_5$–$C_7$cycloalkyl, $C_1$–$C_6$alkylcarbonyl, $C_1$–$C_{20}$alkoxy, phenyl or phenyl-$C_1$–$C_3$alkyl;

m is 1 or 2;

n is 0 or 1;

o is from 0 to 3;

p is 0 or 1;

q is from 0 to 3; and r is 1 or 2.

Of special interest are compounds of formula (1) wherein

Y is chlorine or bromine, m is 1, n is 0 or 1, o is 0, p is 0 or 1, r is 1 or 2, and q is 0.

Of very special interest are compounds of formula (1) wherein

Y is chlorine, m is 1, n is 0, o is 0, p is 0 or 1, q is 0, r is 1 or 2 and p is 0.

Especially preferred are the compounds of formulae (2)

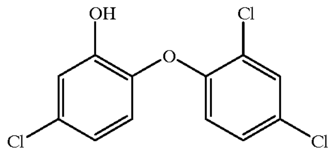

and (3)

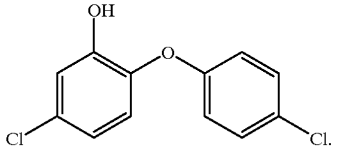

Also of interest are halogen-free diphenyl ethers of formula (1), for example compounds of formula (1) wherein p and r are 0.

Especially preferred compounds accordingly correspond to formula (4)

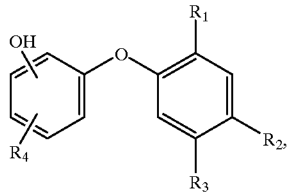

wherein $R_1$ and $R_2$ are each independently of the other hydrogen, $C_1$–$C_{20}$alkyl, $C_5$–$C_7$cycloalkyl, $C_1$–$C_6$alkylcarbonyl, $C_1$–$C_{20}$alkoxy, phenyl or phenyl-$C_1$–$C_3$alkyl;

$R_3$ is hydrogen, $C_1$–$C_{20}$alkyl or $C_1$–$C_{20}$alkoxy;

$R_4$ is hydrogen, $C_1$–$C_{20}$alkyl, hydroxy-substituted $C_1$–$C_{20}$alkyl, $C_5$–$C_7$cycloalkyl, hydroxy, formyl, acetonyl, $C_1$–$C_6$alkylcarbonyl, $C_2$–$C_{20}$alkenyl, carboxy, carboxy-$C_1$–$C_3$alkyl, $C_1$–$C_3$-alkylcarbonyl, $C_1$–$C_3$alkyl or carboxyallyl.

Very especially preferred compounds correspond to formulae (5)

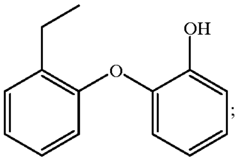
;

(6)

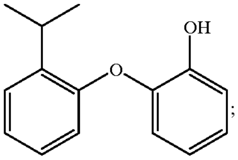
;

(7)

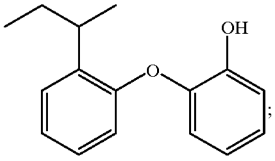
; and (8)

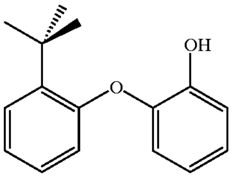
.

The following compounds come into consideration as component (b):

- sulfonates of terpenoids or of mono- or di-nuclear aromatic compounds, e.g. sulfonates of camphor, toluene, xylene, cumene or of naphthol;
- saturated or unsaturated $C_3$–$C_{12}$-di- or -poly-carboxylic acids, e.g. malonic, succinic, glutaric, adipic, pimelic, suberic, azelaic and sebacic acid, undecane- and dodecane-dioic acid, fumaric, maleic, tartaric and malic acid and also citric and aconitic acid;
- aminocarboxylic acids, such as ethylenediaminetetraacetic acid, hydroxyethylethylene-diaminetetraacetic acid and nitrilotriacetic acid;
- cycloaliphatic carboxylic acids, such as camphoric acid;
- aromatic carboxylic acids, such as benzoic, phenylacetic, phenoxyacetic and cinnamic acid, 2-, 3- and 4-hydroxybenzoic acid, anilinic acid, o-, m- and p-chlorophenylacetic acid and o-, m- and p-chlorophenoxyacetic acid;
- isethionic acid;
- tannic acid;
- acid amides of formula (9)

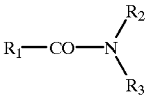
, wherein $R_1$ is hydrogen or $C_1$–$C_{12}$ alkyl and $R_2$ and $R_3$ are each independently of the other hydrogen, $C_1$–$C_{12}$alkyl, $C_2$–$C_{12}$alkenyl, hydroxy-$C_1$–$C_{12}$-alkenyl, hydroxy-$C_2$–$C_{12}$alkyl, or a polyglycol ether chain having from 1 to 30—$CH_2$—$CH_2$—O— or —$CHY_1$—$CHY_2$—O— groupings, wherein one of the radicals $Y_1$ and $Y_2$ is hydrogen and the other is methyl, such as N-methylacetamide;

- urea derivatives of formula (10)

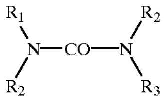
, wherein $R_1$, $R_2$, $R_3$ and $R_4$ are each independently of the others hydrogen, $C_1$–$C_8$alkyl, $C_2$–$C_8$-alkenyl, $C_1$–$C_8$hydroxyalkyl or $C_2$–$C_8$hydroxyalkenyl.

All the organic acids mentioned under (b) can also be in the form of their water-soluble salts, such as the alkali metal salts, especially the sodium or potassium salts or the amine ($NR_1R_2R_3$) salts, wherein $R_1$, $R_2$ and $R_3$ are each independently of the others hydrogen, $C_1$–$C_8$alkyl, $C_2$–$C_8$alkenyl, $C_1$–$C_8$hydroxyalkyl, $C_5$–$C_8$cycloalkyl or polyalkenyleneoxy-$C_1$–$C_{18}$alkyl or $R_1$, $R_2$ and $R_3$ together with the nitrogen atom to which they are bonded form unsubstituted or $C_1$–$C_4$alkyl-substituted morpholino.

Component (b) may be a single compound or may consist of a plurality of different compounds.

Special preference is given to a combination of cumene sulfonate and citric acid monohydrate.

As component (c) there come into consideration anionic, nonionic, cationic and zwitterionic and amphoteric synthetic detergents.

Anionic detergents are

- sulfates, such as, for example, fatty alcohol sulfates, the alkyl chain of which has from 8 to 18 carbon atoms, such as, for example, sulfated lauryl alcohol;
- fatty alcohol ether sulfates, such as, for example, the acid esters or salts thereof of a polyadduct of from 2 to 30 mol of ethylene oxide and 1 mol of a $C_8$–$C_{22}$ fatty alcohol; the alkali metal, ammonium or amine salts of $C_8$–$C_{20}$ fatty acids, referred to as soaps, such as, for example, coconut fatty acid;
- alkylamide sulfates;
- alkylamine sulfates, such as monoethanolamine lauryl sulfate;
- alkylamide ether sulfates;
- alkylryl polyether sulfates;
- monoglyceride sulfates;
- alkanesulfonates, the alkyl chain of which contains from 8 to 20 carbon atoms, e.g. dodecyl sulfonate;
- alkylamide sulfonates;
- alkylaryl sulfonates;
- α-olefin sulfonates;
- sulfosuccinic acid derivatives, such as alkyl sulfosuccinates, alkyl ether sulfosuccinates or alkylsulfosuccinamide derivatives;

N-[alkylamidoalkyl]amino acids of formula (12)

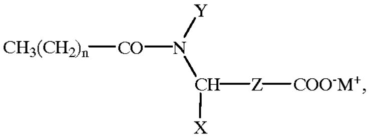

wherein

X is hydrogen, $C_1$–$C_4$alkyl or —COO—$M^+$,

Y is hydrogen or $C_1$–$C_4$alkyl,

Z is $—(CH_2)_{1-1}—$ $m_1$ is from 1 to 5, $n_1$ is an integer from 6 to 18, and M is an alkali metal cation or amine cation, alkyl and alkylaryl ether carboxylates of formula (13) $CH_3$—X—Y—A, wherein X is a radical of formula $—(CH_2)_{5-19}—O—$,

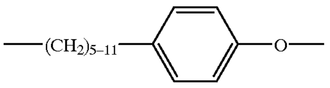

or

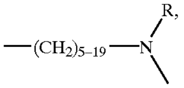

R is hydrogen or $C_1$–$C_4$alkyl,

Y is $—(CHCHO)_{1-50}—$,

A is $(CH_2)_{m2-1}—COO^-M^+$ or

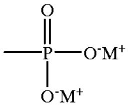

$m_2$ is from 1 to 6 and

M is an alkali metal cation or amine cation.

Also used as anionic surfactants are fatty acid methyl taurides, alkyl isothionates, fatty acid polypeptide condensation products and fatty alcohol phosphoric acid esters. The alkyl radicals occurring in those compounds preferably have from 8 to 24 carbon atoms.

The anionic surfactants are generally in the form of their water-soluble salts, such as the alkali metal, ammonium or amine salts. Examples of such salts include lithium, sodium, potassium, ammonium, triethylamine, ethanolamine, diethanolamine and triethanolamine salts. The sodium, potassium or ammonium ($NR_1R_2R_3$) salts, especially, are used, with $R_1$, $R_2$ and $R_3$ each independently of the others being hydrogen, $C_1$–$C_4$alkyl or $C_1$–$C_4$hydroxy-alkyl.

Especially preferred anionic surfactants in the composition according to the invention are monoethanolamine lauryl sulfate or the alkali metal salts of fatty alcohol sulfates, especially sodium lauryl sulfate and the reaction product of from 2 to 4 mol of ethylene oxide and sodium lauryl ether sulfate.

As zwitterionic and amphoteric surfactants are $C_8$–$C_{18}$betaines, $C_8$–$C_{18}$sulfobetaines, $C_8$–$C_{24}$alkylamido-$C_1$–$C_4$alkylenebetaines, imidazoline carboxylates, alkylamphocarboxylic acids, alkylamphocarboxylic acids (e.g. lauroamphoglycinate) and N-alkyl-β-aminopropionates or -iminodipropionates, with preference being given to $C_{10}$–$C_{20}$alkylamido-$C_1$–$C_4$alkylenebetaines and especially to coconut fatty acid amide propyl betaine.

Nonionic surfactants are, derivatives of the adducts of propylene oxide/ethylene oxide having a molecular weight of from 1000 to 15000, fatty alcohol ethoxylates (1–50 EO), alkylphenol polyglycol ethers (1–50 EO), ethoxylated hydrocarbons, fatty acid glycol partial esters, for example diethylene glycol monostearate, fatty acid alkanolamides and dialkanolamides, fatty acid alkanolamide ethoxylates and fatty amine oxides.

As cationic surfactants are amine oxides, such as, for example, behenamine oxide, cocamidopropylamine oxide, cocamine oxide, coco-morpholine oxide, decylamine oxide, decyl/tetradecylamine oxide, diaminopyrimidine oxide, dihydroxyethyl-$C_8$–$C_{10}$alkoxypropylamine oxide, dihydroxyethyl-$C_9$–$C_{11}$alkoxypropylamine oxide, dihydroxyethyl-$C_{12}$–$C_{15}$alkoxypropylamine oxide, dihydroxyethylcocamine oxide, dihydroxyethyllauramine oxide, dihydroxyethylstearamine oxide, dihydroxyethyl tallow amine oxide, hydrogenated tallow amine oxide, hydroxyethyl/hydroxypropyl-$C_{12}$–$C_{15}$alkoxypropyl-amine oxide, isostearamidopropylamine oxide, isostearamidopropylmorpholine oxide, lauramidopropylamine oxide, lauramine oxide, methylmorpholine oxide, myristamidopropylamine oxide, myristamine oxide, myristyl/cetyl amine oxide, oleamidopropylamine oxide, oleamine oxide, olivamidopropylamine oxide, palmitamidopropylamine oxide, palmitamine oxides, PEG-3-lauramine oxide, sesamidopropylamine oxide, soyamido-propylamine oxides, stearamidopropylamine oxide, stearamine oxide, tallow amidopropyl-amine oxide, tallow amine oxide and undecyleneamidopropylamine oxide.

Preference is given to the use of cocamine oxides and lauramine oxides.

As component (c) there may also be used the salts of saturated and unsaturated $C_8$–$C_{22}$ fatty acids either alone or in the form of a mixture with one another or in the form of a mixture with other detergents mentioned as component (c). Examples of such fatty acids include, for example, capric acid, lauric acid, myristic acid, palmitic acid, stearic acid, arachidic, behenic, caproleic, dodecenoic, tetradecenoic, octadecenoic, oleic, eicosenoic and erucic acid, and the commercial mixtures of such acids, such as, for example, coconut fatty acid. Such acids are present in the form of salts, there coming into consideration as cations alkali metal cations, such as sodium and potassium cations, metal atoms, such as zinc and aluminium atoms, and sufficiently basic nitrogen-containing organic compounds, such as amines and ethoxylated amines. Such salts may also be prepared in situ.

As component (d) there come into consideration as dihydric alcohols especially those compounds having from 2 to 6 carbon atoms in the alkylene moiety, such as ethylene glycol, 1,2- or 1,3-propanediol, 1,3-, 1,4- or 2,3-butanediol, 1,5-pentanediol and 1,6-hexanediol.

Preference is given to 1,2-propanediol (propylene glycol).

Preferred monohydric alcohols are ethanol, n-propanol and isopropanol and mixtures of those alcohols.

The pH value of the composition according to the invention is from 3 to 10, preferably from 3.5 to 5.5.

The compositions according to the invention in the form of soap or syndet solutions may also comprise customary additives, such as sequestering agents, colorants, perfume oils, thikkening or solidifying agents (consistency regulators), emollients, UV absorbers, skin-protective agents, antioxidants, additives that improve the mechanical properties, such as dicarboxylic acids and/or aluminium, zinc, calcium and magnesium salts of $C_{14}$–$C_{22}$fatty acids, and optionally preservatives.

Soap compositions according to the invention can be prepared by mixing components (a) and (b), (c) and optionally (d) in any desired order with the requisite amount of deionised water and stirring the mixture until homogeneous. The mixture is made up to 100% with tap water or deionised water. This is a purely physical procedure. No chemical reaction takes place between the individual components.

The formulations according to the invention exhibit strong bactericidal activity in two respects:

rapid destruction of germs present.

This can be demonstrated, for example, by a suspension test, e.g. according to test method EN 1276.

long-term bactericidal activity on the treated surface, as a result of which repopulation is prevented effectively.

This can be demonstrated, for example, by the AATCC 100-1993 method.

For disinfecting and cleaning human skin and hands and hard objects, the soap compositions according to the invention can be applied thereto in dilute or undiluted form, an amount of at least 2 ml, preferably in the undiluted form, coming into consideration for disinfection of the hands.

The soap compositions according to the invention are also used in washing and cleaning formulations, such as, for example, in liquid, household and powder detergents or in softeners for textile fibre materials.

The fibre materials are undyed or dyed or printed fibre materials, for example of silk, wool, polyamide or polyurethanes, and especially cellulosic fibre materials of all kinds. Such fibre materials are, for example, natural cellulose fibres, such as cotton, linen, jute and hemp, as well as cellulose and regenerated cellulose. Preferred suitable textile fibre materials are of cotton.

The following Examples illustrate the invention. Percentages and parts are percentages and parts by weight.

EXAMPLE 1

All-purpose Cleaner for Dilute Application

Composition 0.6% compound of formula (101)

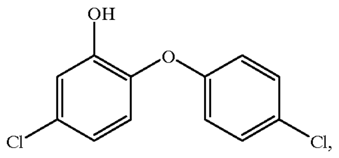

1.0% cocamidopropylbetaine,
3.0% lauramine oxide,
6.0% sodium lauryl sulfate,
4.0% sodium citrate,
3.0% sodium carbonate,
3.0% ethanol,
5.0% sodium cumene sulfonate,
water ad 100.0%.

The compound of formula (101) is dissolved at 40° C. in a mixture of the cocamidopropylbetaine, lauramine oxide, sodium lauryl sulfate and 90% of the calculated amount of water. The remaining constituents are added at room temperature and the mixture is stirred until homogeneous.

Bactericidal Activity of the Formulation According to EN 1276 (Concentration 80%, Contact Time 5 Minutes) in Log Reduction Test Principle 1.0 ml of a bacterial suspension is added to 8.0 ml of the formulation (the test concentration is multiplied by a factor of 1.25) and to 1.0 ml of a suspension of 0.3% (factor 10) of bovine albumin and mixed vigorously. After the contact time (see above) at 21° C. (+/−1° C.), a 0.1 ml sample is removed and added to 50 ml of TSB+inactivator (=test neutralisation mixture, 10°). 500 $\mu$l of the neutralisation mixture are added to 9 ml of TSB+inactivator to give a $10^{-2}$ dilution. Each test neutralisation mixture and the dilutions are filtered over a membrane and washed with 150 ml of distilled water. The membranes are incubated for 48 hours on the surface of agar plates. After incubation, the colonies are counted and set out in a Table, and the log reduction is calculated.

Evaluation of the neutralisation reveals good inactivation in respect of all the germs tested.

| Results (in log reduction): | |
|---|---|
| *Staphylococcus aureus* ATCC 6538 | >5 |
| *Escherichia coli* ATCC 10536 | >5 |
| *Enterococcus hirae* ATCC 10541 | >5 |
| *Pseudomonas aeruginosa* ATCC 15442 | >5 |

Bactericidal Activity on Ceramic Plates According to AATCC 100-1993

Treatment of the ceramic plates

The ceramic plates (35×35 mm) are sprayed with a 1:80 dilute solution of the all-purpose cleaner (3 sprays). The sprayed plate is wiped with a paper cloth impregnated with the dilution.

Test Principle

Ceramic plates (~35×35 mm) are placed in sterile Petri dishes (diameter: 55 mm). All the samples are then inoculated with 0.25 ml of a bacterial suspension (approx. ~$10^5$ cfu/-sample) and placed in a humidity chamber at 37° C.

Directly after inoculation and after 2, 4 and 24 hours at 37° C., the inoculated ceramic plates are placed in 50 ml of 0.07 molar phospate buffer (pH 7.4, containing 1% Tween 80 and 0.3% lecithin) and shaken for 1 minute. After shaking, a dilution gradient to a concentration of $10^{-2}$ in sterile distilled water is prepared. 100 $\mu$l samples of the undiluted solution and of the $10^{-1}$ und $10^{-2}$ dilutions are applied to the plates in the form of a coating using a spiralometer. After incubation, the surviving colonies are counted, calculated as KBE/sample and set out in

TABLE 1

| | Results (KBE/sample) | | | |
|---|---|---|---|---|
| | 0 | 2 h | 4 h | 24 h |
| | *Staphylococcus aureus* ATCC 9144 | | | |
| Ceramic plate treated with all-purpose cleaner containing 0.6% of the compound of formula (101) (1:80 dilution) | $3.2 \times 10^5$<br>$3.4 \times 10^5$ | $2.4 \times 10^5$<br>$4.1 \times 10^5$ | $4.1 \times 10^5$<br>$3.7 \times 10^5$ | <100<br><100 |
| Ceramic plate treated with the all-purpose cleaner without the | $2.7 \times 10^5$<br>$2.9 \times 10^5$ | $2.8 \times 10^5$<br>$2.4 \times 10^5$ | $1.6 \times 10^5$<br>$1.7 \times 10^5$ | <100<br><100 |

TABLE 1-continued

| | Results (KBE/sample) | | | |
|---|---|---|---|---|
| | 0 | 2 h | 4 h | 24 h |
| compound of formula (101) (1:80 dilution) | | | | |
| Sample | Klebsiella pneumoniae ATCC 4352 | | | |
| Ceramic plate treated with all-purpose | $3.4 \times 10^5$<br>$3.5 \times 10^5$ | $1.0 \times 10^5$<br>$1.3 \times 10^5$ | $6.7 \times 10^4$<br>$7.5 \times 10^4$ | <100<br><100 |

TABLE 1-continued

| | Results (KBE/sample) | | | |
|---|---|---|---|---|
| | 0 | 2 h | 4 h | 24 h |
| cleaner containing 0.6% of the compound of formula (101) (1:80 dilution) | | | | |
| Ceramic plate treated with all-purpose cleaner without the compound of formula (101) (1:80 dilution) | $3.6 \times 10^5$<br>$3.4 \times 10^5$ | $9.1 \times 10^5$<br>$1.0 \times 10^5$ | $5.6 \times 10^5$<br>$5.8 \times 10^5$ | $1.5 \times 10^5$<br>$1.6 \times 10^5$ |

EXAMPLE 2

All-purpose Cleaner for Dilute Application

Composition 0.6% compound of formula (101)
10.0% sodium lauryl sulfate,
5.0% citric acid,
5.0% PPG-2 methyl ether
5.0% sodium cumene sulfonate,
water ad 100.0%

Bactericidal Activity of the Formulation According to EN 1276 (Concentration 80%, Contact Time 5 Minutes) in Log Reduction

| Results: | |
|---|---|
| *Staphylococcus aureus* ATCC 6538 | >5 |
| *Escherichia coli* ATCC 10536 | >5 |
| *Enterococcus hirae* ATCC 10541 | >5 |
| *Pseudomonas aeruginosa* ATCC 15442 | >5 |
| 10% dilution | |
| *Staphylococcus aureus* ATCC 6538 | >3 |
| *Escherichia coli* ATCC 10536 | 3 |
| *Enterococcus hirae* ATCC 10541 | >3 |
| *Pseudomonas aeruginosa* ATCC 15442 | 3 |

EXAMPLE 3

Dish-washing Agent

| Formulation number:<br>Composition: | 1<br>in % g/g | 2<br>in % g/g | 3<br>in % g/g | 4<br>in % g/g | 5<br>in % g/g |
|---|---|---|---|---|---|
| compound of formula (101) | 0.6 | 0.6 | 0.6 | 0.6 | 0.6 |
| sodium $C_{14-17}$alkyl sec-sulfonate | 10.00 | 10.00 | 10.00 | 10.00 | — |
| sodium lauryl sulfate | 20.00 | 20.00 | 20.00 | 15.00 | — |
| sodium laureth sulfate | — | — | — | — | 15 |
| sodium dodecyl benzenesulfonate | — | — | — | — | 5.3 |
| laureth-08 | 3.00 | 3.00 | — | — | — |
| laureth-09 | — | — | 3.00 | 2.00 | — |
| ethanol | 5.00 | 5.00 | — | — | — |
| sodium cumene sulfonate | 5.00 | 3.00 | 5.00 | 5.00 | 5.00 |
| citric acid | 5.00 | 3.00 | 3.00 | 3.00 | 3.00 |
| benzoic acid | 0.50 | — | — | — | 0.50 |
| sodium chloride | — | — | 3.00 | 3.00 | 1.0 |
| sodium sulfate | — | — | — | — | 3.5 |
| water | ad 100 | ad 100 | ad 100 | ad 100 | ad 100 |
| pH value | 5.0 | 5.0 | 5.0 | 5.0 | 5.0 |

Bactericidal Activity of the Formulation According to EN 1276 (Concentration 80%, Contact Time 5 Minutes) in Log Reduction

| Formulation number | 1 | 2 | 3 | 4 | 5 |
|---|---|---|---|---|---|
| *Staphylococcus aureus* ATCC 6538 | >5 | >5 | >5 | >5 | >5 |
| *Escherichia coli* ATCC 10536 | >5 | >5 | >5 | >5 | 5 |
| *Enterococcus hirae* ATCC 10541 | >5 | >5 | >5 | >5 | >5 |
| *Pseudomonas aeruginosa* ATCC 15442 | >5 | >5 | >5 | >5 | >5 |

Bactericidal Activity on Sponges According to AATCC 100-1993 Treatment of the Sponge Cloths 1 ml of dish-washing agent is applied to a sponge cloth (10×10 cm) and treated for 1 minute. The sponge cloth is then rinsed in 5 liters of water and dried overnight. Circles of 2 cm diameter are stamped out from the sponge cloth.

Test Principle

Sponge disks of a diameter of 20 mm are placed in sterile Petri dishes (diameter: 55 mm). All the samples are then inoculated with 0.25 ml of a bacterial suspension (approx. ~$10^5$ cfu/sample) and placed in a humidity chamber at 37° C.

Directly after inoculation and after 2, 4 and 24 hours at 37° C., the inoculated sponge disks are placed in 50 ml of 0.07 molar phosphate buffer (pH 7.4, containing 1% Tween 80 and 0.3% lecithin) and shaken for 1 minute. After shaking, a dilution gradient to $10^{-2}$ in sterile distilled water is prepared. 100 $\mu$l samples of the undiluted solutions and of the $10^{-1}$ and $10^{-2}$ dilutions are applied in the form of a coating to the surface of suitable nutrient medium using a spiralometer and cultivated for 48 hours at 37° C. After incubation, the surviving colonies are counted, calculated as KBE/sample and set out in Table 2:

TABLE 2

| Samples | Results (KBE/sample) 0 | 2 h | 4 h | 24 h |
|---|---|---|---|---|
| Test germ → | *Staphylococcus aureus* ATCC 9144 | | | |
| Sponge treated with dish-washing agent No. 4 containing 0.6% of the compound of formula (101) | $2.7 \times 10^5$<br>$3.2 \times 10^5$ | $3.0 \times 10^3$<br>$3.0 \times 10^3$ | <100<br><100 | <100<br><100 |
| Sponge treated with dish-washing agent No. 4 placebo without the compound of formula (101) | $4.3 \times 10^5$<br>$4.8 \times 10^5$ | $2.6 \times 10^5$<br>$3.6 \times 10^5$ | $3.2 \times 10^5$<br>$3.0 \times 10^5$ | $4.3 \times 10^7$<br>$4.0 \times 10^7$ |
| Test germ → | *Escherichia coli* NCTC 8196 | | | |
| Sponge treated with dish-washing agent No. 4 containing 0.6% of the compound of formula (101) | $5.8 \times 10^5$<br>$5.8 \times 10^5$ | $7.1 \times 10^5$<br>$6.1 \times 10^3$ | <100<br><100 | <100<br><100 |
| Sponge treated with dish-washing agent No. 4 placebo without the compound of formula (101) | $5.7 \times 10^5$<br>$6.0 \times 10^5$ | $1.2 \times 10^6$<br>$1.3 \times 10^6$ | $3.2 \times 10^5$<br>$3.0 \times 10^5$ | $5.6 \times 10^7$<br>$59 \times 10^7$ |

The results show that the sponges treated according to the invention suppress the bacteria effectively.

EXAMPLE 4

Detergent

| Composition | % by weight |
|---|---|
| compound of formula (101) | 0.6 |
| sodium dodecyl benzenesulfonate | 15.0 |
| pareth 45-7 | 14.0 |
| ethanol | 9.0 |
| soap slivers | 10.0 |
| trisodium citrate | 4.0 |
| triethanolamine | 5.0 |
| tinopal CBS-X | 0.1 |
| water | ad 100 |
| pH value | 10 |

The compound of formula (101) is dissolved in sodium dodecyl benzenesulfonate, pareth 45-7 and ethanol.

Soap, trisodium citrate, triethanolamine and the calculated amount of water are stirred at 60° C. until a clear solution forms.

The soap solution is added to the solution of the compound of formula (101).

Tinopal CBS-X is added and dissolved.

The formulation is made up to 100% with water.

Bactericidal Activity on Washed Cotton Fabric

Washing of the Cotton Fabric

| Washing conditions (Lini test): | |
|---|---|
| Detergent: | 99/07/05A and 99/07/05A placebo |
| Detergent concentration: | 2.3 g of detergent/300 ml of water |
| Liquor: | 1:10 |
| Fabric: | 30 g of cotton |
| Washing temperature: | 40° C. |

-continued

| Washing conditions (Lini test): | |
|---|---|
| Rinsing: | 2 × 30 seconds (in 1 liter of water) |
| Drying: | at 30° C. until dry |

Test Principle

Cotton circles of a diameter of 20 mm are placed in sterile Petri dishes (diameter: 55 mm). All the samples are then inoculated with 0.25 ml of a bacterial suspension (approx. ~$10^5$ cfu/sample) and placed in a humidity chamber at 37° C.

Directly after inoculation and after 4, 8 and 24 hours at 37° C., the inoculated cotton circles are placed in 50 ml of 0.07 molar phosphate buffer (pH 7.4, containing 1% Tween 80 and 0.3% lecithin) and shaken for 1 minute. After shaking, a dilution gradient to $10^{-2}$ in sterile distilled water is prepared. 100 $\mu$l samples of the undiluted solutions and of the $10^{-1}$ and $10^{-2}$ dilutions are applied in the form of a coating to the surface of suitable nutrient medium using a spiralometer and cultivated for 48 hours at 37° C. After incubation, the surviving colonies are counted, calculated as KBE/sample and set out in Table 3:

TABLE 3

| Samples | 0 | 4 h | 8 h | 24 h |
|---|---|---|---|---|
| Test germ → | *Staphylococcus aureus* ATCC 9144 | | | |
| Cotton washed with liquid detergent containing 0.6% of the compound of formula (101) (99/07/05A) | $2.5 \times 10^5$<br>$2.2 \times 10^5$ | $1.7 \times 10^3$<br>$1.9 \times 10^3$ | $9.1 \times 10^3$<br>$1.7 \times 10^4$ | <100<br><100 |
| Cotton washed with liquid detergent that does not contain 0.6% of the compound of formula (101) (99/07/05A placebo) | $2.6 \times 10^5$<br>$2.1 \times 10^5$ | $1.1 \times 10^6$<br>$9.4 \times 10^5$ | $4.7 \times 10^7$<br>$5.0 \times 10^7$ | $1.8 \times 10^9$<br>$2.0 \times 10^9$ |
| Test germ → | *Klebsiella pneumoniae* ATCC 4352 | | | |
| Cotton washed with liquid detergent containing 0.6% of the compound of formula (101) (99/07/05A) | $1.3 \times 10^5$<br>$7.7 \times 10^4$ | $4.3 \times 10^3$<br>$5.3 \times 10^3$ | $6.1 \times 10^2$<br><100 | <100<br><100 |
| Cotton washed with liquid detergent contain the compound of formula (101) (99/07/05A placebo) | $8.4 \times 10^4$<br>$7.9 \times 10^4$ | $2.6 \times 10^6$<br>$2.5 \times 10^6$ | $1.2 \times 10^8$<br>$1.4 \times 10^8$ | $3.2 \times 10^9$<br>$2.8 \times 10^9$ |

The results show that the cotton samples treated according to the invention suppress the bacteria effectively.

What is claimed is:

1. A surface-active surfactant composition containing (a) from 0.01 to 2% by weight of an antimicrobial active ingredient from the class of diphenyl ethers, (b) from 0.1 to 30% by weight of a hydrotropic agent comprising a combination of cumene sulfonate and citric acid monohydrate, (c) from 6.0 to 50% by weight of one or more synthetic detergents or soaps or a combination of said substances, (d) a monohydric or dihydric alcohol, and (e) tap water or deionised water ad 100%.

2. A composition according to claim 1 wherein said component (a) is a hydroxydiphenyl ether of the general formula (1)

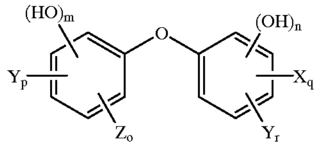

wherein

Y is chlorine or bromine,

X is $C_1$–$C_{20}$alkyl, hydroxy-substituted $C_1$–$C_{20}$alkyl, $C_5$–$C_7$cycloalkyl, hydroxy, formyl, acetonyl, $C_1$–$C_6$alkylcarbonyl, $C_2$–$C_{20}$alkenyl, carboxy, carboxy-$C_1$–$C_3$alkyl or carboxyallyl;

Z is hydrogen, hydroxy, $C_1$–$C_{20}$alkyl, $C_5$–$C_7$cycloalkyl, $C_1$–$C_6$alkylcarbonyl, $C_1$–$C_{20}$alkoxy, phenyl or phenyl-$C_1$–$C_3$alkyl;

m is 1 or 2;

n is 1 or 1;

o is from 0 to 3;

p is 0 or 1;

q is from 0 to 3; and r is 1 or 2.

3. A composition according to claim 2, wherein said component (a) is a compound of formula (1) wherein Y is chlorine or bromine, m is 1, n is 0 or 1, o is 0, p is 0 or 1, r is 1 or 2, and q is 0.

4. A composition according to claim 2, wherein said component (a) is a compound of formula (1) wherein Y is chlorine, m is 1, n is 0, o is 0, p is 0 or 1, q is 0, r is 1 or 2 and p is 0.

5. A composition according to claim 4, wherein said component (a) is a compound of formula (2)

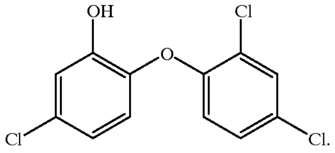

6. A composition according to claim 4, wherein said component (a) is a compound of formula (3)

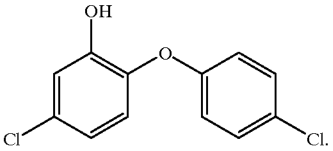

7. A composition according to claim 1, wherein said component (a) is a compound of formula (4)

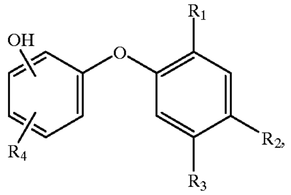

wherein $R_1$ and $R_2$ are each independently of the other hydrogen, $C_1$–$C_{20}$alkyl, $C_5$–$C_7$cycloalkyl, $C_1$–$C_6$alkylcarbonyl, $C_1$–$C_{20}$alkoxy, phenyl or phenyl-$C_1$–$C_3$alkyl;

$R_3$ is hydrogen, $C_1$–$C_{20}$alkyl or $C_1$–$C_{20}$alkoxy;

$R_4$ is hydrogen, $C_1$–$C_{20}$alkyl, hydroxy-substituted $C_1$–$C_{20}$alkyl, $C_5$–$C_7$cycloalkyl, hydroxy, formyl, acetonyl, $C_1$–$C_6$alkylcarbonyl, $C_2$–$C_{20}$alkenyl, carboxy, carboxy-$C_1$–$C_3$alkyl, $C_1$–$C_3$-alkylcarbonyl, $C_1$–$C_3$alkyl or carboxyallyl.

8. A composition according to claim 1, wherein as anionic surfactant (component (c)) there is used a fatty alcohol sulfate, the alkyl chain of which has from 8 to 18 carbon atoms.

9. A composition according to claim 8, wherein said component (c) is the alkali metal salt of sulfated lauryl alcohol or monoethanolamine lauryl sulfate.

10. A composition according to claim 1, wherein said component (c) is $C_{10}$–$C_{20}$alkylamido-$C_1$–$C_4$alkylenebetaine.

11. A composition according to claim 1, wherein as salt of a saturated and/or unsaturated $C_8$–$C_{22}$ fatty acid according to component (c) there is used lauric, myristic, palmitic, stearic, arachidic, behenic, caproleic, dodecenoic, tetradecenoic, octadecenoic, oleic, eicosenoic or erucic acid.

12. A composition according to claim 1, wherein said component (d) is propylene glycol.

13. A composition according to claim 1, wherein said component (d) is ethanol, propanol, isopropanol or a mixture of those alcohols.

14. A method for disinfecting and cleaning human skin and hands and hard objects comprising treating human skin and hands and hard objects with the antimicrobial composition according to claim 1.

15. A method for washing and cleaning of textile fiber materials comprising treating the fibers with a detergent formulation containing the antimicrobial composition according to claim 1.

* * * * *